United States Patent
Tanoury et al.

(12)

(10) Patent No.: US 6,472,563 B1
(45) Date of Patent: Oct. 29, 2002

(54) FORMOTEROL TARTRATE PROCESS AND POLYMORPH

(75) Inventors: Gerald J. Tanoury, Hudson; Chris H. Senanayake, Shrewsbury; Donald W Kessler, Groton, all of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 10/037,183

(22) Filed: Nov. 9, 2001

(51) Int. Cl.$^7$ ............... C07C 231/20; C07C 233/03; A61K 31/16
(52) U.S. Cl. ............... 564/216; 564/220; 564/221; 514/629; 514/630
(58) Field of Search ............... 564/216, 220, 564/221; 514/629, 630

(56) References Cited

U.S. PATENT DOCUMENTS

| 5,434,304 A | * 7/1995 | Trofast et al. ............... 564/221 |
| 6,268,533 B1 | 7/2001 | Gao et al. ............... 564/216 |

FOREIGN PATENT DOCUMENTS

| EP | 390762 | 10/1990 |
| ES | 2005492 | 3/1989 |
| ES | 2031407 | 12/1992 |
| WO | WO92/05147 | 4/1992 |
| WO | WO00/21487 | 4/2000 |

OTHER PUBLICATIONS

Hett et al. "Large Scale Synthesis of Enatio–and Diastereomerically Pure (R,R)–Formoterol" *Organic Proc. Res. & Dev.* 2, 96–99 (1998).

Hett et al. "Conformational Toolbox of Oxazaborolidine Catalysts in the Enantioselective . . . " *Tet. Lett.* 39, 1705–1708 (1998).

Hett et al. "Enantio– and Diastereoselective Synthesis of all Four Stereoisomers of Formoterol" *Tet. Lett.* 38, 1125–1128 (1997).

Murase et al. "New Beta–Adrenoreceptor Stimulants Studies on 3–Acylamino–4–hydroxy– . . . " *Chem. Pharm. Bull.* 25(6), 1368–1377 (1977).

Murase et al. "Absolute Configuration of Four Isomers of 3–Formamido–4–hydroxy– . . . " *Chem. Pharm. Bull.* 26(4), 1123–1129 (1978).

Trofast et al. "Steric Aspects of Agonism and Antagonism at Beta–Adrenoceptors: Synthesis . . . " *Chirality* 3, 443–450 (1991).

Kurihara et al. (–)–+–Formoterol, a Selective Beta 2–Adrenoreceptor Agonist: *Acta Cryst. C53*, 1887–1889 (1997).

* cited by examiner

*Primary Examiner*—Shailendra Kumar
(74) *Attorney, Agent, or Firm*—Heslin Rothenberg Farley & Mesiti P.C.; Philip E. Hansen

(57) ABSTRACT

A method of preparation of a highly pure salt of R,R-formoterol L-tartrate is disclosed. The process provides the most thermodynamically stable polymorph by recrystallization of a novel polymorph.

14 Claims, 9 Drawing Sheets

FORMOTEROL TARTRATE PROCESS AND POLYMORPH

FIELD OF THE INVENTION

The present invention relates to a method of preparation of a highly pure salt of optically pure formoterol and to a polymorph thereof.

BACKGROUND OF THE INVENTION

Formoterol, whose chemical name is (+/−)N-[2-hydroxy-5-[1-hydroxy-2 [[2-(p-methoxyphenyl)-2-propyl]amino] ethyl]phenyl]-formamide, is a highly potent and $\beta_2$-selective adrenoceptor agonist having a long lasting bronchodilating effect when inhaled. The structure of formoterol is as shown:

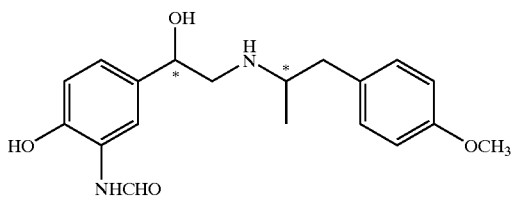

Formoterol has two chiral centers in the molecule, each of which can exist in two possible configurations. This gives rise to four combinations: (R,R), (S,S), (R,S) and (S,R). (R,R) and (S,S) are mirror images of each other and are therefore enantiomers; (R,S) and (S,R) are similarly an enantiomeric pair. The mirror images of (R,R) and (S,S) are not, however, superimposable on (R,S) and (S,R), which are diastereomers. Formoterol is presently available commercially only as a racemic diastereomer, (R,R) plus (S,S) in a 1:1 ratio, and the generic name formoterol refers to this enantiomeric mixture. The racemic mixture that is commercially available for administration is a dihydrate of the fumarate salt. The order of potency of the isomers is (R,R)>>(R,S)=(S,R)>(S,S), and the (R,R)-isomer is 1000-fold more potent than the (S,S)-isomer. Administration of the pure (R,R)-isomer also offers an improved therapeutic ratio. U.S. Pat. No. 6,268,533 and PCT application WO 00/21487 disclose that the L-(+)-tartrate salt of R,R-formoterol is unexpectedly superior to other salts of R,R-formoterol, being easy to handle, pharmaceutically innocuous and non-hygroscopic.

The polymorphic behavior of drugs can be of crucial importance in pharmacy and pharmacology. Polymorphs are, by definition, crystals of the same molecule having different physical properties as a result of the order of the molecules in the crystal lattice. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g. tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing: for example, one polymorph might be more likely to form solvates or might be difficult to filter and wash free of impurities (i.e. particle shape and size distribution might be different between one polymorph relative to the other).

Each pharmaceutical compound has an optimal therapeutic blood concentration and a lethal concentration. The bio-availability of the compound determines the dosage strength in the drug formulation necessary to obtain the ideal blood level. If the drug can crystallize as two or more polymorphs differing in bio-availability, the optimal dose will depend on the polymorph present in the formulation. Some drugs show a narrow margin between therapeutic and lethal concentrations. Chloramphenicol-3-palmitate (CAPP), for example, is a broad spectrum antibiotic known to crystallize in at least three polymorphic forms and one amorphous form. The most stable form, A, is marketed. The difference in bio-activity between this polymorph and another form B, is a factor of eight-creating the possibility of fatal overdosages of the compound if unwittingly administered as form B due to alterations during processing and/or storage. Therefore, regulatory agencies, such as the US Food and Drug Administration, have begun to place tight controls on the polymorphic content of the active component in solid dosage forms. In general, for drugs that exist in polymorphic forms, if anything other than the pure, thermodynamically preferred polymorph is to be marketed, the regulatory agency will require batch-by-batch monitoring. Thus, it becomes important for both medical and commercial reasons to produce and market the pure drug in its most thermodynamically stable polymorph, substantially free of other kinetically favored polymorphs.

U.S. Pat. No. 6,268,533, which is incorporated herein by reference, discloses that the L-(+)-tartrate salt of R,R-formoterol exists in two polymorphic forms. We have now discovered a third polymorphic form of (R,R)-formoterol L-tartrate. As a result of its unique solubility properties, this third polymorph provides an opportunity for a greatly improved process for obtaining highly pure (R,R)-formoterol L-tartrate in its most thermodyamically stable polymorphic form.

SUMMARY OF THE INVENTION

In one aspect the invention relates to (R,R)-formoterol L-tartrate in the form of a crystalline solid comprising at least 95% of a polymorph having peaks at the diffraction degrees with the intensity shown below in an X-ray powder diffraction pattern:

| Polymorph C | | |
|---|---|---|
| Peak number | 2-Theta | Intensity |
| 1 | 6.4 | 100.0 |
| 2 | 9.0 | 14.4 |
| 3 | 11.1 | 14.8 |
| 4 | 12.4 | 13.9 |
| 5 | 12.9 | 19.7 |
| 6 | 13.5 | 19.5 |
| 7 | 14.0 | 15.1 |
| 8 | 15.0 | 19.7 |
| 9 | 15.4 | 16.9 |
| 10 | 15.7 | 18.1 |
| 11 | 16.3 | 12.8 |

-continued

Polymorph C

| Peak number | 2-Theta | Intensity |
|---|---|---|
| 12 | 17.5 | 64.9 |
| 13 | 19.4 | 47.3 |
| 14 | 19.9 | 44.8 |
| 15 | 21.3 | 29.3 |
| 16 | 22.3 | 31.5 |
| 17 | 22.9 | 35.8 |
| 18 | 24.1 | 80.0 |
| 19 | 24.7 | 17.6 |
| 20 | 25.5 | 11.3 |
| 21 | 26.0 | 15.6 |
| 22 | 26.8 | 9.1 |
| 23 | 27.4 | 8.5 |
| 24 | 28.4 | 10.8 |
| 25 | 29.0 | 8.5 |
| 26 | 30.5 | 8.1 |
| 27 | 32.7 | 10.9 |
| 28 | 34.2 | 7.9 |
| 29 | 35.7 | 9.3 |
| 30 | 36.4 | 6.6 |
| 31 | 37.3 | 7.9 |
| 32 | 37.8 | 9.1 |
| 33 | 39.3 | 10.0 |
| 34 | 39.6 | 11.4 |
| 35 | 41.1 | 5.7 |
| 36 | 42.3 | 4.7 |

Henceforth, this 36-peak polymorph, which has not been previously described in the literature, will be referred to as "polymorph C".

In another aspect, the invention relates to a process for producing this new polymorph. The process comprises stirring a slurry of polymorph (B) in water, isopropyl alcohol and at least 13% by weight toluene at 40–55° C.

The discovery of polymorph C and its physical properties gives rise to the third aspect of the invention: a process for the preparation of highly pure (R,R)-formoterol L-tartrate. In its most fundamental embodiment, the process involves crystallizing polymorph C from aqueous isopropyl alcohol. This produces (R,R)-formoterol L-tartrate of a chemical purity heretofore unattainable.

Another aspect of the invention is then the (R,R)-formoterol L-tartrate produced by this process. The (R,R)-formoterol L-tartrate resulting from the inventive process is in the form of a crystalline solid comprising at least 95% of the most thermodynamically stable polymorph of (R,R)-formoterol L-tartrate. This polymorph, which will henceforth be referred to as polymorph A, has 23 peaks at the diffraction degrees with the intensity shown in the following X-ray powder diffraction pattern:

Polymorph A

| peak number | 2-Theta | Intensity |
|---|---|---|
| 1 | 8.8 | 33.1 |
| 2 | 9.3 | 33.4 |
| 3 | 12.1 | 58.1 |
| 4 | 12.4 | 60.6 |
| 5 | 14.2 | 30.9 |
| 6 | 15.2 | 87.4 |
| 7 | 15.5 | 82.8 |
| 8 | 16.8 | 69.8 |
| 9 | 18.9 | 39.6 |
| 10 | 19.7 | 41.1 |

-continued

Polymorph A

| peak number | 2-Theta | Intensity |
|---|---|---|
| 11 | 20.8 | 40.6 |
| 12 | 22.5 | 38.8 |
| 13 | 23.0 | 59.9 |
| 14 | 23.7 | 100.0 |
| 15 | 25.6 | 55.9 |
| 16 | 26.8 | 37.2 |
| 17 | 28.6 | 25.6 |
| 18 | 30.9 | 37.2 |
| 19 | 36.1 | 28.0 |
| 20 | 38.1 | 25.0 |
| 21 | 39.1 | 22.7 |
| 22 | 41.5 | 21.3 |
| 23 | 43.3 | 20.9 |

(R,R)-formoterol L-tartrate, predominantly in the polymorphic form A is known and described in U.S. Pat. No 6,268,533. However, even in its chemically purest state, material described in the '533 patent contains from 0.2 to 1.5% by weight of chemical impurities, one of which is desformoterol L-tartrate. (R,R)formoterol L-tartrate cannot be purified to contain less than 0.2% by weight of any impurity, except by the process of the instant application, employing the hitherto unknown polymorph C.

In another aspect the invention relates to a method for preventing bronchoconstriction or inducing bronchodilation in a mammal by administering the pure polymorph A. Pure, in the sense used herein, means containing less than 5% of other polymorphs of (R,R)-formoterol L-tartrate, less than 0.5% of other chemical impurities and less than 2% of other optical isomers of formoterol.

In another aspect the invention relates to pharmaceutical compositions comprising a pharmaceutically acceptable carrier and pure polymorph A of R,R-formoterol L-(+)-tartrate.

BRIEF DESCRIPTION OF THE DRAWINGS

Various aspects of the invention will become more readily apparent upon reference to the following description when taken in conjunction with the accompanying drawings, in which.

DETAILED DESCRIPTION OF THE INVENTION

Figure 1:
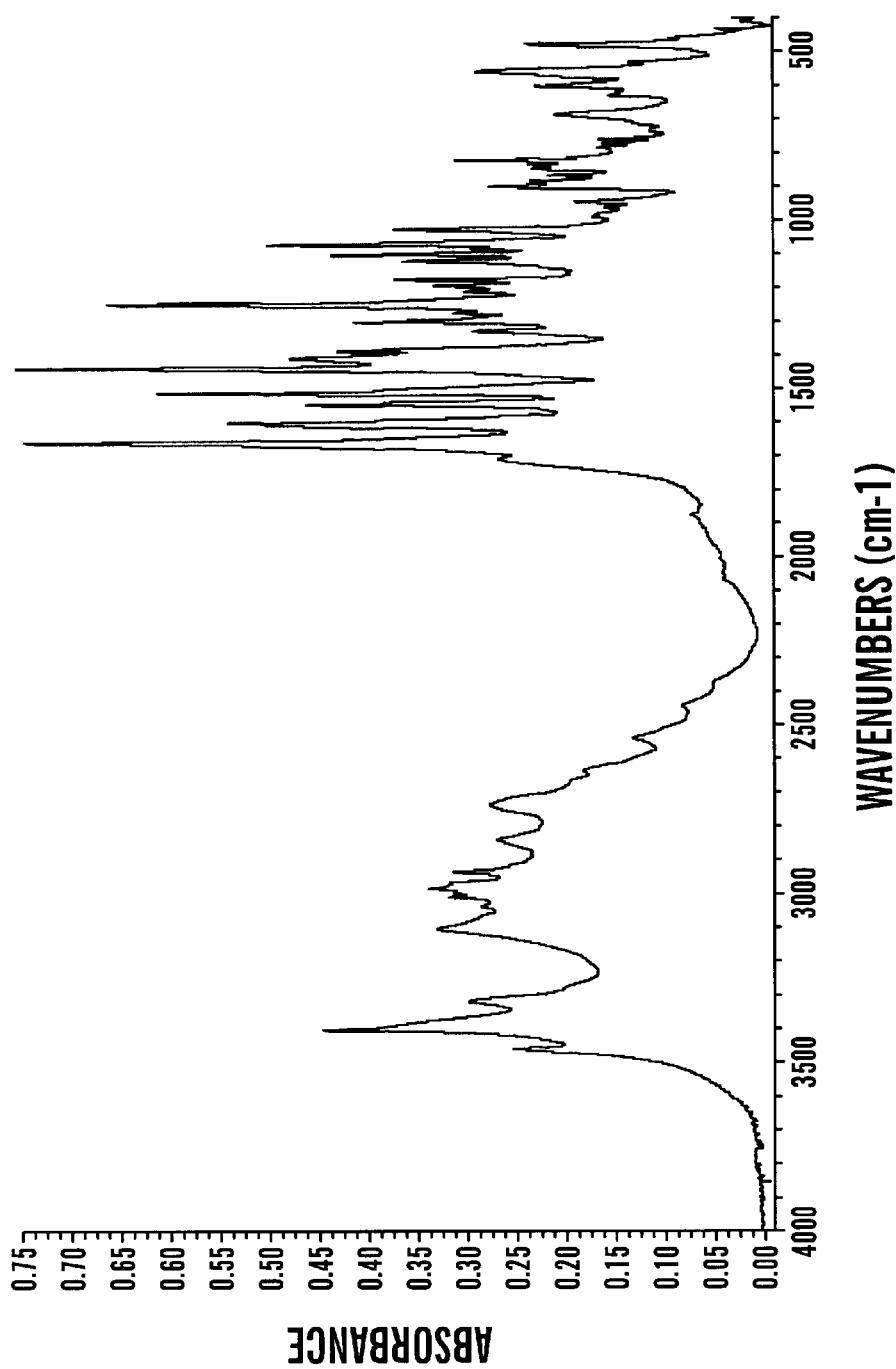
FIG. 1 is an IR spectrum of R,R-formoterol L-(+)-tartrate, polymorph B.

Two reports have been published describing the synthesis of all four isomers of formoterol. In the first report [Murase et al. op. cit.], the (R,R)- and (S,S)-isomers were obtained by diastereomeric crystallization of racemic formoterol with tartaric acid. In the second report [Trofast et al. op. cit.], racemic 4-benzyloxy-3-nitrostyrene oxide was coupled with an optically pure (R,R)- or (S,S)-N-(1-phenylethyl)-N-(1-(p-methoxyphenyl)-2-propyl)amine to give a diastereomeric mixture of formoterol precursors, which were then separated by semipreparative HPLC and transformed to the pure formoterol isomers. Both syntheses suffer long synthetic procedure and low overall yield and are impractical for large scale production of optically pure (R,R)- or (S,S)-formoterol. For example, the Trofast reference describes reacting 4.5 grams of the styrene oxide with 4.8 grams of the phenethylamine to produce 94 milligrams of the pure S,S enantiomer. The only practical, economical and efficient method for synthesizing optically pure formoterol is described in U.S. Pat. No. 6,268,533 and PCT application WO 00/21487. The synthesis is outlined in Scheme I:

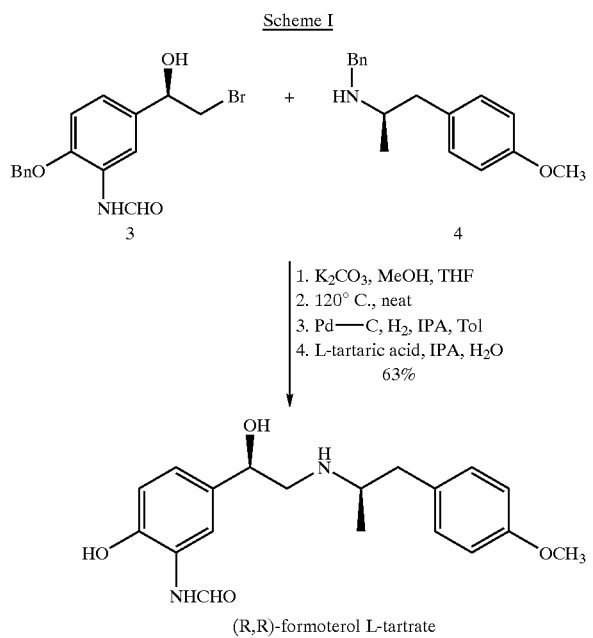

Scheme I

1. $K_2CO_3$, MeOH, THF
2. 120° C., neat
3. Pd—C, $H_2$, IPA, Tol
4. L-tartaric acid, IPA, $H_2O$
63%

(R,R)-formoterol L-tartrate

This synthesis initially produces the kinetically favored polymorph, which will be referred to hereafter as polymorph B. Polymorph B exhibits 30 peaks at the diffraction degrees with the intensity shown below in an X-ray powder diffraction pattern:

| Polymorph B | | |
|---|---|---|
| peak number | 2-Theta | Intensity |
| 1 | 6.7 | 29.8 |
| 2 | 7.7 | 23.9 |
| 3 | 8.5 | 76.8 |
| 4 | 9.9 | 24.1 |
| 5 | 11.6 | 23.7 |
| 6 | 12.2 | 35.9 |
| 7 | 13.0 | 24.8 |
| 8 | 13.7 | 32.7 |
| 9 | 16.4 | 32.9 |
| 10 | 17.3 | 99.1 |
| 11 | 19.4 | 47.9 |
| 12 | 20.6 | 100.0 |

| -continued | | |
|---|---|---|
| Polymorph B | | |
| peak number | 2-Theta | Intensity |
| 13 | 22.1 | 72.8 |
| 14 | 22.7 | 70.2 |
| 15 | 23.5 | 29.1 |
| 16 | 23.9 | 25.0 |
| 17 | 24.5 | 22.8 |
| 18 | 25.4 | 35.8 |
| 19 | 25.5 | 39.8 |
| 20 | 26.3 | 48.0 |
| 21 | 27.4 | 25.7 |
| 22 | 28.6 | 28.6 |
| 23 | 29.5 | 20.5 |
| 24 | 30.9 | 20.1 |
| 25 | 33.0 | 19.5 |
| 26 | 37.2 | 22.1 |
| 27 | 38.6 | 20.1 |
| 28 | 40.9 | 19.7 |
| 29 | 41.7 | 20.0 |
| 30 | 44.3 | 20.0 |

(R,R)-formoterol L-tartrate, in the polymorphic form B is known and described in U.S. Pat. No. 6,268,533.

As the (R,R)-formoterol L-tartrate separates in the initial crystallization from this process, it is predominantly in the kinetically favored form, polymorph B. Polymorph B is referred to in the '533 patent as P2. In pure form it exhibits a peak at about 179° C. on differential scanning calorimetry and is soluble in water at 25° C. to the extent of 26.7 mg/mL. U.S. Pat. No. 6,268,533 describes the conversion of B to the thermodynamically most stable polymorphic form A. Polymorph A is referred to in the '533 patent as P1. Polymorph A exhibits a peak at about 193° C. on differential scanning calorimetry and is soluble in water at 25° C. to the extent of 15.4 mg/mL. However, the product described in '533, as it initially crystallizes, contains four identified chemical impurities (described below), and, no matter how many times the product is recrystallized, the resulting polymorph A contains at least 0.5% impurities. While not wishing to be held to any particular theory, applicants surmise that the conditions of recrystallization may result in the partial hydrolysis of the formamide to the amine:

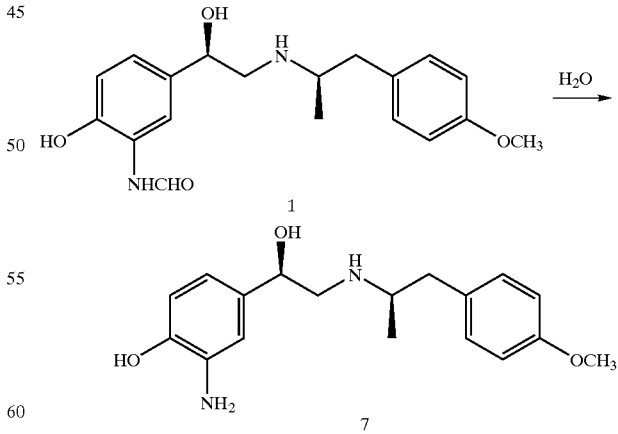

Whatever the reason may be, the process described in the literature cannot be made to produce (R,R)-formoterol L-tartrate polymorph A containing less than 0.5% impurities. The conundrum of purification was already recognized in U.S. Pat. No. 6,268,533, which states, "To obtain (R,R)

formoterol L-tartrate of the highest chemical and optical purity, it is necessary that one not recrystallize P1 [polymorph A]. P1 is the more thermodynamically stable form and is preferred for formulations, but because of its lower solubility, it requires higher temperatures and longer times to dissolve in the recrystallization solvent. As a result, some degradation occurs and impurities are introduced in the recrystallization process."

A solution to the chemical purity problem has now been found. The answer lies in the existence and properties of a newly discovered third polymorph, polymorph C.

In developing a process for production of (R,R)-formoterol L-tartrate as an active pharmaceutical ingredient (API), two factors are of great importance: the impurity profile and the crystal morphology of the API. The results from preliminary development work showed that the impurity profile of the API consisted of impurities 7 and 8 whose abundances ranged from 0.2 to 1.5%, and that traditional crystallization methods could not decrease the level of 7 below 0.2%. This preliminary work also indicated that the isolation and crystallization conditions yielded perhaps as many as three polymorphic forms of the API. The requirements for the API necessitated levels of 7 and 8 below 0.2% and, as explained above, the API had to be in the most thermodynamically stable crystal form. The difficulty in controlling the level of 7 and the polymorphic nature of the API required the development of a process for the production of (R,R)-formoterol L-tartrate to provide the requisite purity and the proper crystal form.

Initial studies characterized the impurity profile of isolated intermediates and the API at various stages in the process. As shown in Scheme 1, the crude product was isolated as the tartrate salt from a four step process that entailed epoxide formation, epoxide opening, debenzylation, and salt formation. Before addition of L-tartaric acid, the crude free-base, as a homogeneous solution in isopropyl alcohol/toluene, contained 25–30% total impurities (HPLC). After addition of an aqueous solution of L-tartaric acid, a thick slurry formed, and the isolated crude crystalline product contained four major impurities 7–10 totalling 1% (Table 1).

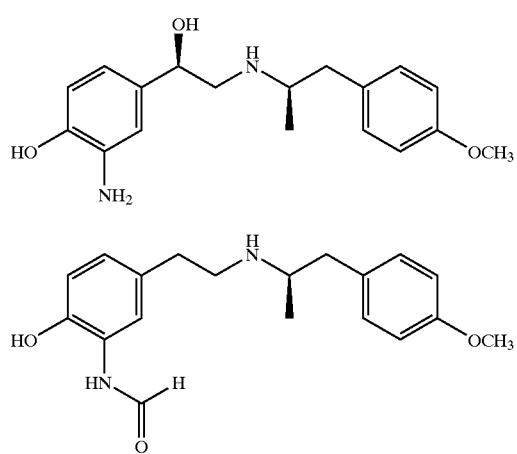

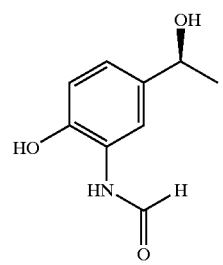

9

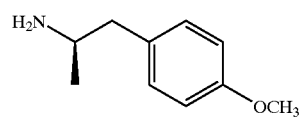

10

A reasonable hypothesis is that aniline 7 was formed by hydrolysis of the formamide group of 1, while 8 was generated as a result of dehydroxylation, and compounds 9 and 10 were formed by hydrogenation of the starting bromohydrin 3 and amine 4, respectively, excess reactants from the previous synthetic steps. After crystallization of the crude solid from 25% aqueous isopropyl alcohol, impurities 9 and 10 were removed, the level of 8 decreased from 0.6% to 0.3%, and the level of 7 increased from 0.1% to 0.2%. The increase in the level of 7 during the crystallization indicated that purification of the API must be restricted to only one recrystallization of the crude wet-cake. Because the preceding steps in the process had been optimized, an improvement in the purity of the final product rested solely on an improvement in the isolation and crystallization of the wet-cake and final product, respectively.

TABLE 1

Impurity Profiles of (R,R)-formoterol L-tartrate Isolated Product*

| Entry | Isolation | 1 (A %) | 7 (A %) | 8 (A %) | 9 (A %) | 10 (A %) |
|---|---|---|---|---|---|---|
| 1 | Isolated crude product | 99.0 | 0.1 | 0.6 | 0.2 | 0.1 |
| 2 | Crystallization of isolated crude | 99.4 | 0.2 | 0.3 | nd | nd |

*Determined by HPLC analysis

After many trials it was unexpectedly discovered that when the slurry of the crude product was warmed to 45–50° C. for 1–5 hr, as shown in Table 2, impurities 9 and 10 were completely removed, and the levels of 7 and 8 were lowered to 0.04 and 0.11%, respectively. After crystallization of the purified crude product following this warming step, the levels of 7 and 8 were easily within the required ranges: 0.12% for 7 and 0.05% for 8. Although the level of 7 rose by 0.08% upon recrystallization, its low initial level allowed the final level to fall below 0.2%. The results are shown in Table 2

TABLE 2

Impurity Profiles of (R,R)-formoterol L-tartrate Isolated Product*

| Entry | Isolation | 1 (A %) | 7 (A %) | 8 (A %) | 9 (A %) | 10 (A %) |
|---|---|---|---|---|---|---|
| 1 | isolated crude product | 99.01 | 0.11 | 0.64 | 0.12 | 0.04 |
| 2 | isolated purified crude product | 99.85 | 0.04 | 0.11 | nd | nd |
| 3 | crystallization of purified crude | 99.83 | 0.12 | 0.05 | nd | nd |

*Determined by HPLC analysis

The thickening of the slurry during the period at 45–50° C. suggested that a polymorph interconversion might have occurred during the impurity removal. This prompted an investigation into the polymorphic modifications of (R,R)-formoterol L-tartrate. Initial examination of the morphology of (R,R)-formoterol L-tartrate identified three distinct crystal forms: forms A, B, and C. The polymorphs were identified at three stages of the process: (1) the crude crystalline solid generated after addition of L-tartaric acid to a solution of the crude free-base (crystal form B), (2) the crystalline solid formed after warming the slurry of the crude solid to effect the impurity removal (crystal form C), and (3) the crystalline solid isolated after crystallization of the crude wet-cake from 25% aqueous isopropyl alcohol (crystal form A). Polymorphs A and B had been observed before, and were reported in the US patent cited above. Polymorph C had never before been observed. Using the protocol created for the impurity removal (vide supra), the three polymorphs could be generated and interconverted according to Scheme II, demonstrating the concurrency of the impurity removal and polymorph interconversion.

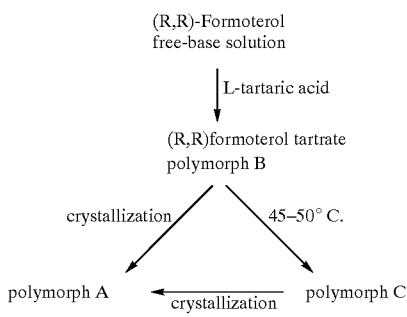

Scheme II

Addition of L-tartaric acid to the reaction solution generated from the four step through-process protocol generated a slurry of (R,R)-formoterol L-tartrate. Filtration of the slurry, followed by rinsing the isolated white solid with isopropyl alcohol, gave the morphologically distinct crystalline solid (R,R)-formoterol L-tartrate/form B. FIG. 1 shows the IR spectrum (KBr pellet), the DSC trace, and the X-ray powder pattern spectrum for the cystalline solid. The most distinct feature of the IR spectrum is the absorbance pattern at 2400–3600 $cm^{-1}$, especially the triplet pattern centered at 3400 $cm^{31\ 1}$. In the DSC trace, the sharpness of the endotherm peak at 177° C. is particularly noteworthy, and in the X-ray powder diffraction spectrum, three sharp singlets and one doublet are the main features of the pattern. The solid isolated at this stage in the process provided a stable crystalline white solid that could be stored for long periods (months) without decomposition.

Figure 2:
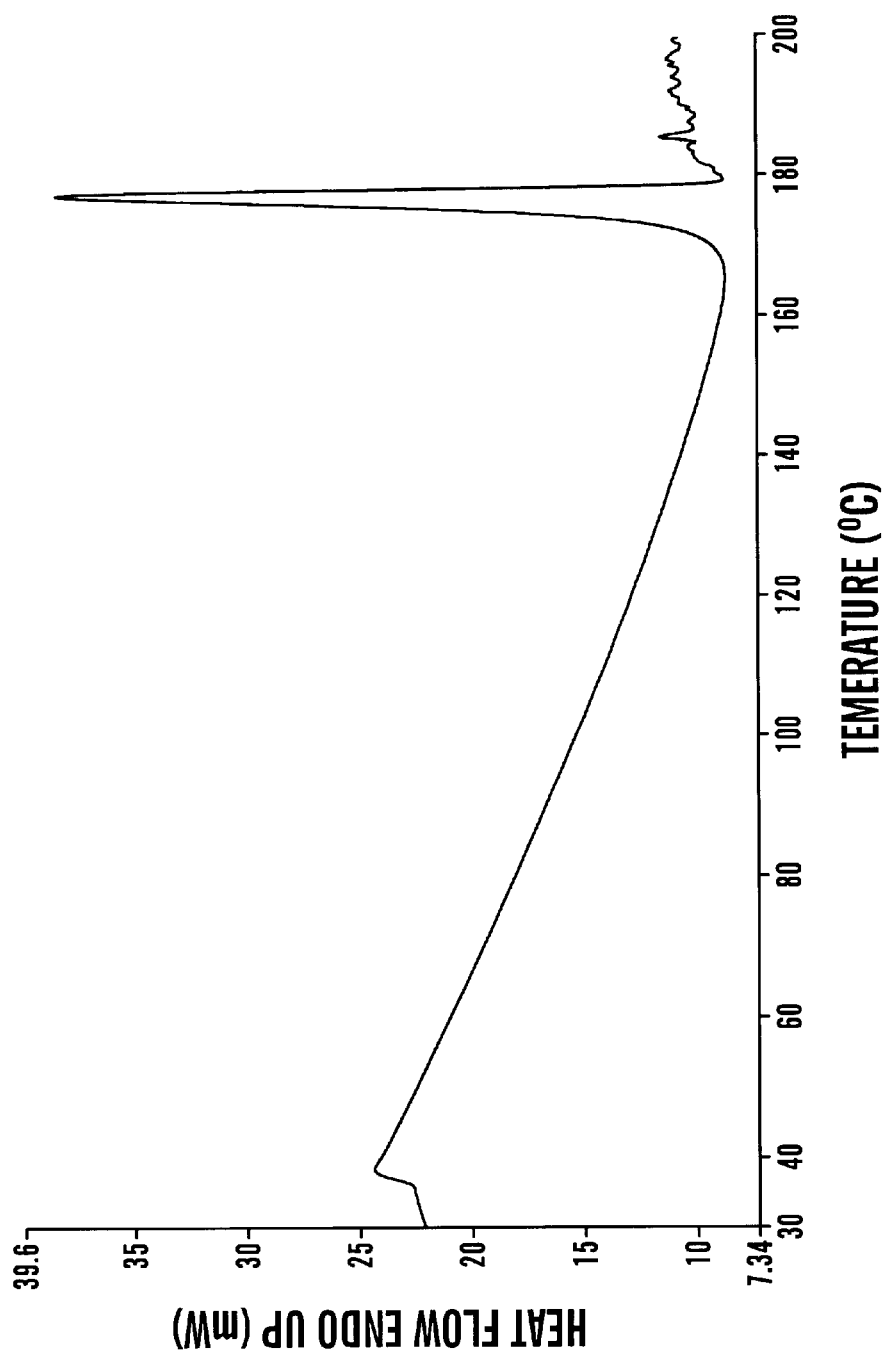
FIG. 2 is a differential scanning calorimetric (DSC) trace of R,R-formoterol L-(+)-tartrate, polymorph B.

When the resultant slurry from the through-process protocol was warmed to 45–50° C. for 1–5 hrs prior to filtration, the slurry thickened. After cooling to room temperature and filtering, a white crystalline solid, polymorph C was isolated. FIG. 2 shows the IR spectrum (KBr pellet), the DSC trace, and the X-ray powder pattern spectrum for this cystalline solid. A comparison of these data with the data presented in FIG. 1 clearly indicates that this solid has a unique polymorphic form. In the IR spectrum, the most readily noticeable pattern is in the 2200–3800 $cm^{-1}$ region. The sharp peaks at approximately 3500 and 3350 $cm^{-1}$ are characteristic of this polymorphic form and contrast sharply with the triplet pattern shown in FIG. 1. Additionally, two very weak transitions at 155 and 167° C. in the DSC trace contrast with the sharp peak at 177° C. shown in FIG. 1. The X-ray powder diffraction spectrum definitively proves that this crystalline solid is morphologically unique when compared to polymorph B. The pattern is characterized by three sharp singlets and one doublet, but the shifts of these peaks are clearly different from those obtained for form B. The conversion of form B to form C was effected by warming the slurry (in the mixture of isopropyl alcohol, water and toluene) to 45–50° C. and holding it at that temperature.

The dependance of the process on the solvent system was studied. Generation of the crude product in crystal form B occurred by addition of an aqueous solution of L-tartaric acid to a solution of the free-base in a 3.7:1 (w/w) isopropyl alcohol:toluene solvent mixture. After addition of tartaric acid, the resultant slurry consisted of a 17 wt % mixture of (R,R)-formoterol tartrate/form B in a 3.7:1.0:2.0 (w/w/w) isopropyl alcohol:toluene:water solvent mixture. The conversion of form B to form C was effected in this solvent mixture. The isolated crude solid in crystal form B was suspended in a 1.8:1 w/w mixture of isopropyl alcohol:water at a concentration of 17 wt %, warmed to 45–50° C., and the conversion to form C and the impurity levels were monitored as a function of the amount of toluene in the solvent mixture (Table 3). When the slurry was warmed to 45–50° C. for an extended period, no polymorph conversion was observed, nor was an impurity removal effected, when the amount of toluene in solution was 9 wt % or lower (entries 1–3). However, when the level of toluene was raised to 13 wt %, the impurity removal was observed (entry 4). Further analysis of this sample showed that conversion to crystal form C occurred also. The same results were observed when the level of toluene was raised to 15 wt % (entry 5). The data show that 13 wt % or more of toluene in the solvent mixture was necessary to cause the impurity removal and polymorph interconversion. We did not establish an upper limit, but practical considerations suggest that, while one could accomplish the conversion and purification with up to 75% toluene, amounts over 15% would add to the expense of solvent and to the problems of disposal without affording a concomitant advantage.

TABLE 3

Impurity Removal from Crude (R,R)-FmTA at 45° C. in 70:30 w/w IPA/Water*

| Entry | Toluene (wt %) | Temp (° C.) | Time (h) | (R,R)-FmTA[1] (A %) | 7[1] (A %) | 8[1] (A %) |
|---|---|---|---|---|---|---|
| 1 | 1 | 44.3 | 20 | 99.24 | 0.04 | 0.73 |
| 2 | 5 | 44.3 | 21 | 99.21 | 0.05 | 0.73 |
| 3 | 9 | 44.1 | 22 | 99.21 | 0.06 | 0.72 |
| 4 | 13 | 45.1 | 24 | 99.82 | 0.04 | 0.10 |
| 5 | 15 | 45.2 | 26 | 99.77 | 0.00 | 0.14 |

*FmTA concentration: 17 wt %, initially crystal form B.
[1]Determined by HPLC.

Figure 3:
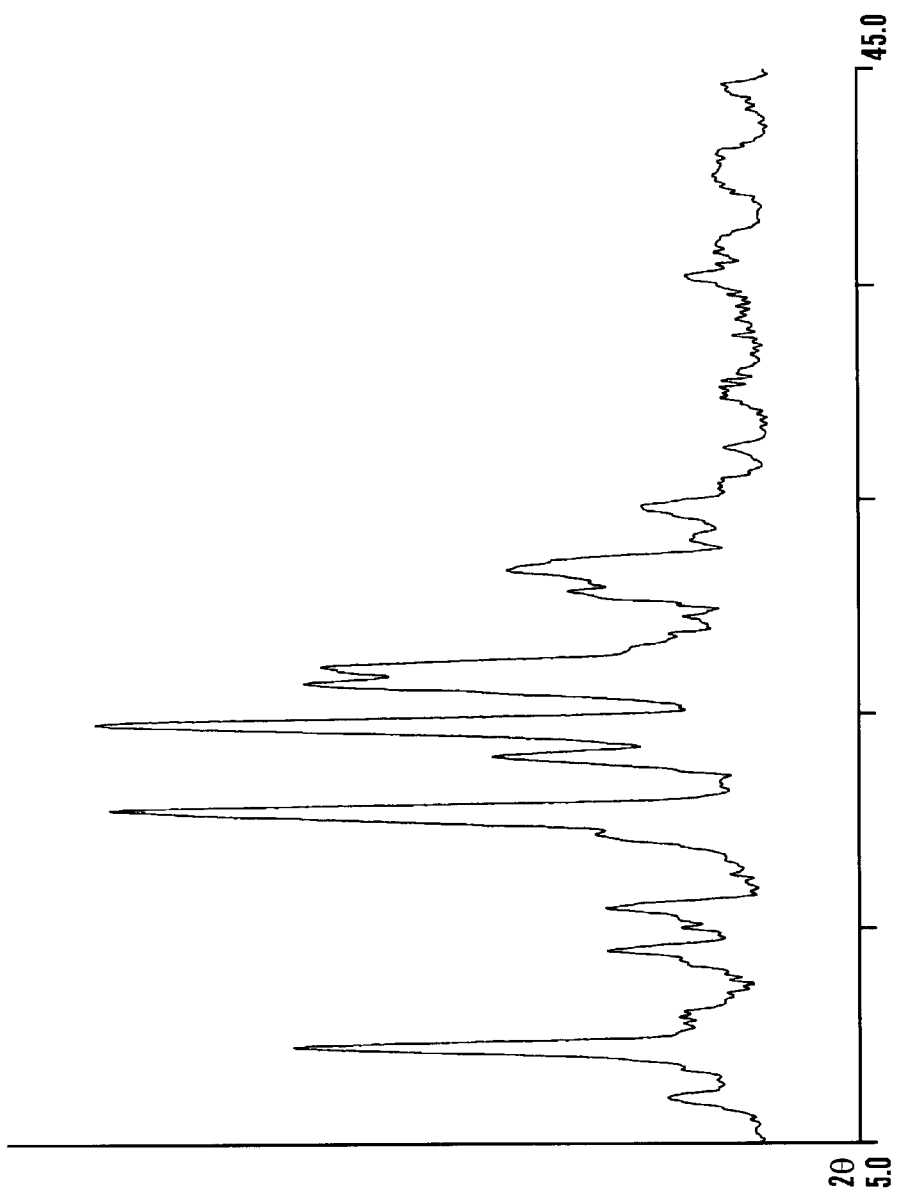
FIG. 3 is an x-ray powder diffraction pattern (XRDP) trace of R,R-formoterol L-(+)-tartrate, polymorph B.
Figure 4:
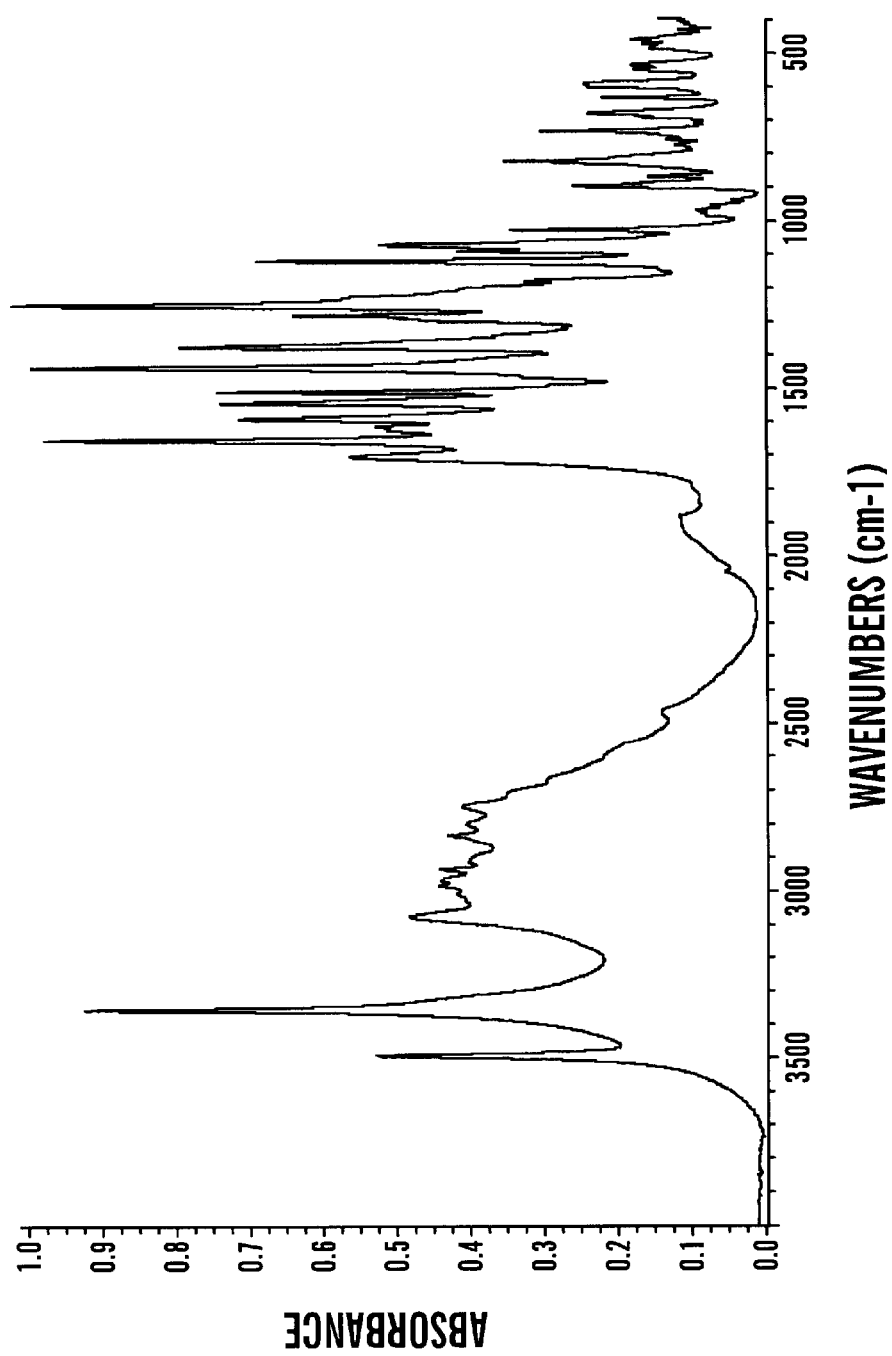
FIG. 4 is an IR spectrum of R,R-formoterol L-(+)-tartrate, polymorph C.
Figure 5:
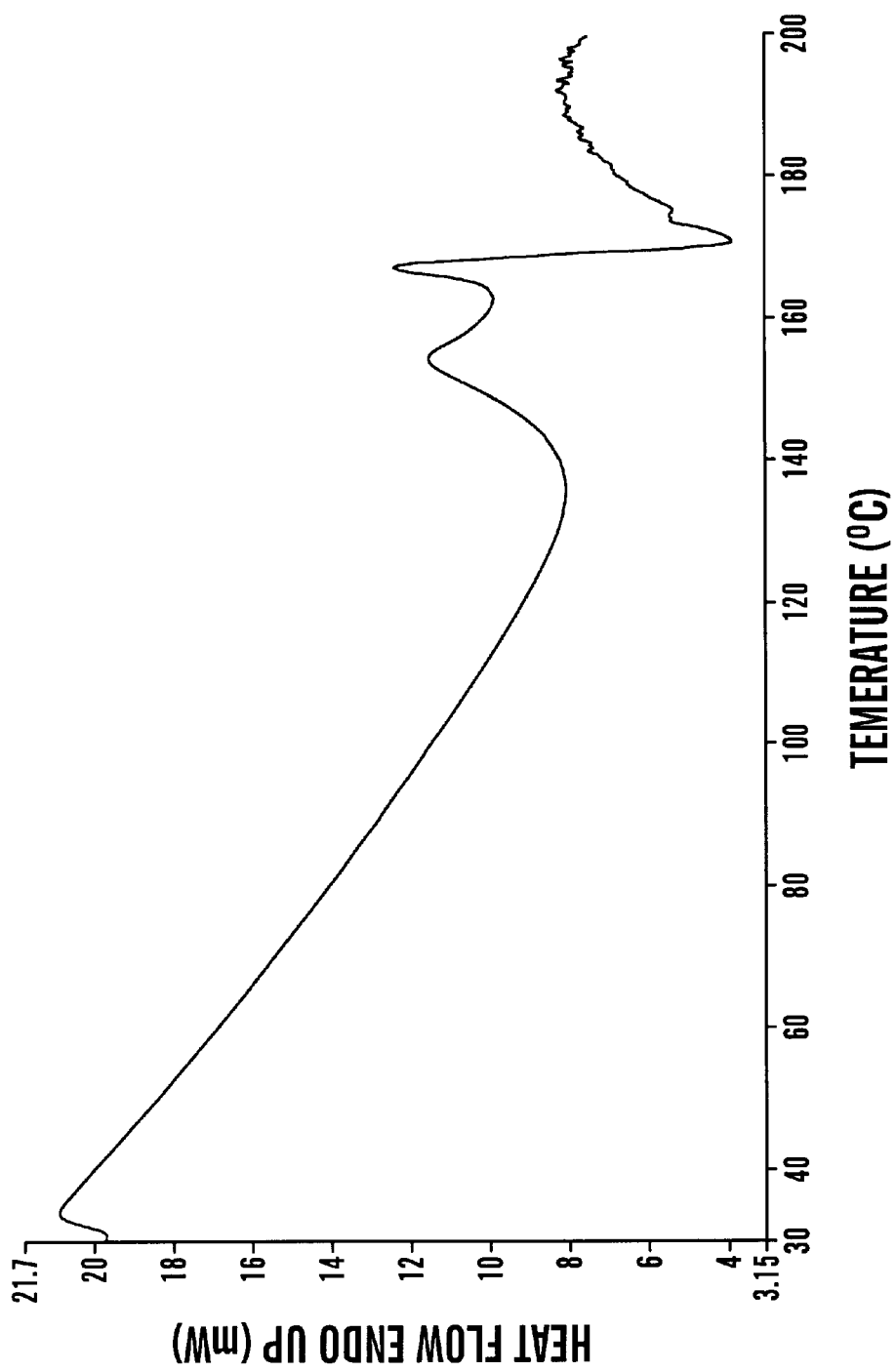
FIG. 5 is a differential scanning calorimetric (DSC) trace of R,R-formoterol L-(+)-tartrate, polymorph C.
Figure 6:
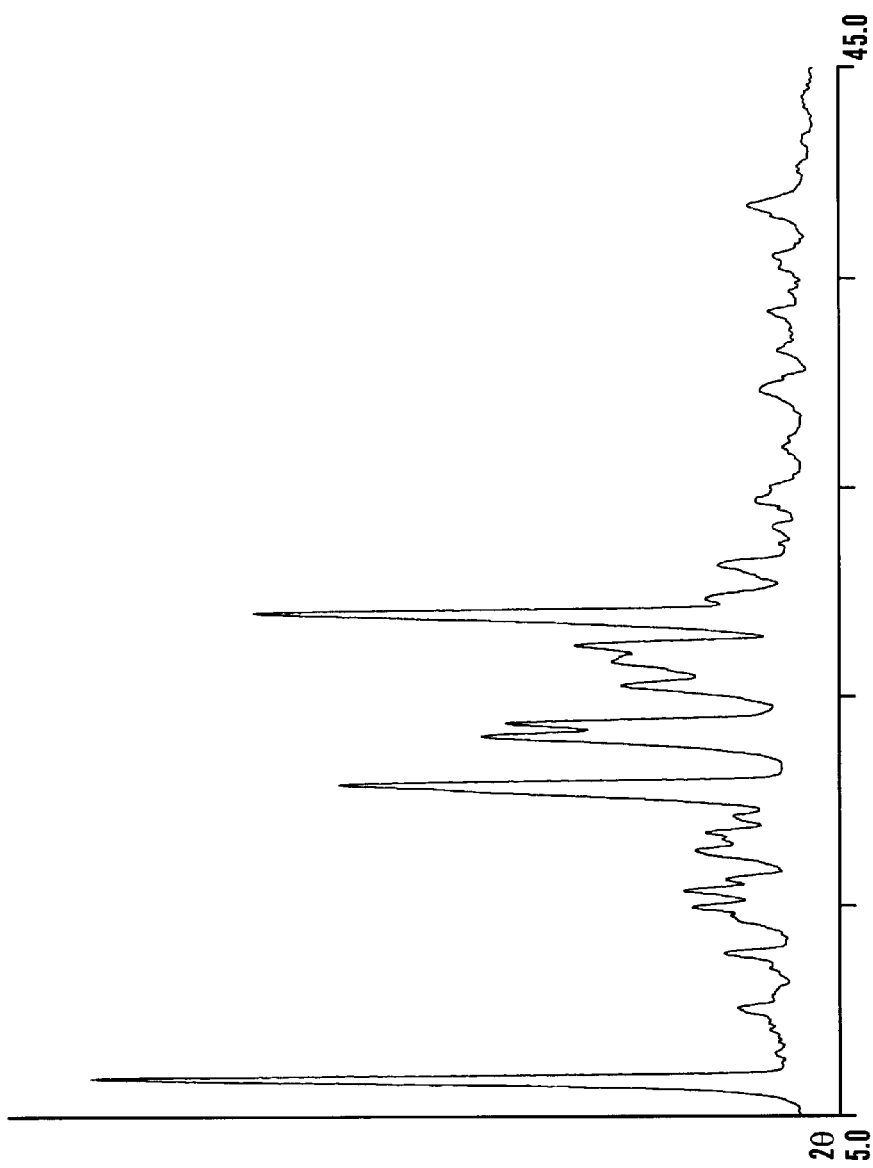
FIG. 6 is an x-ray powder diffraction pattern (XRDP) trace of R,R-formoterol L-(+)-tartrate, polymorph C.
Figure 7:
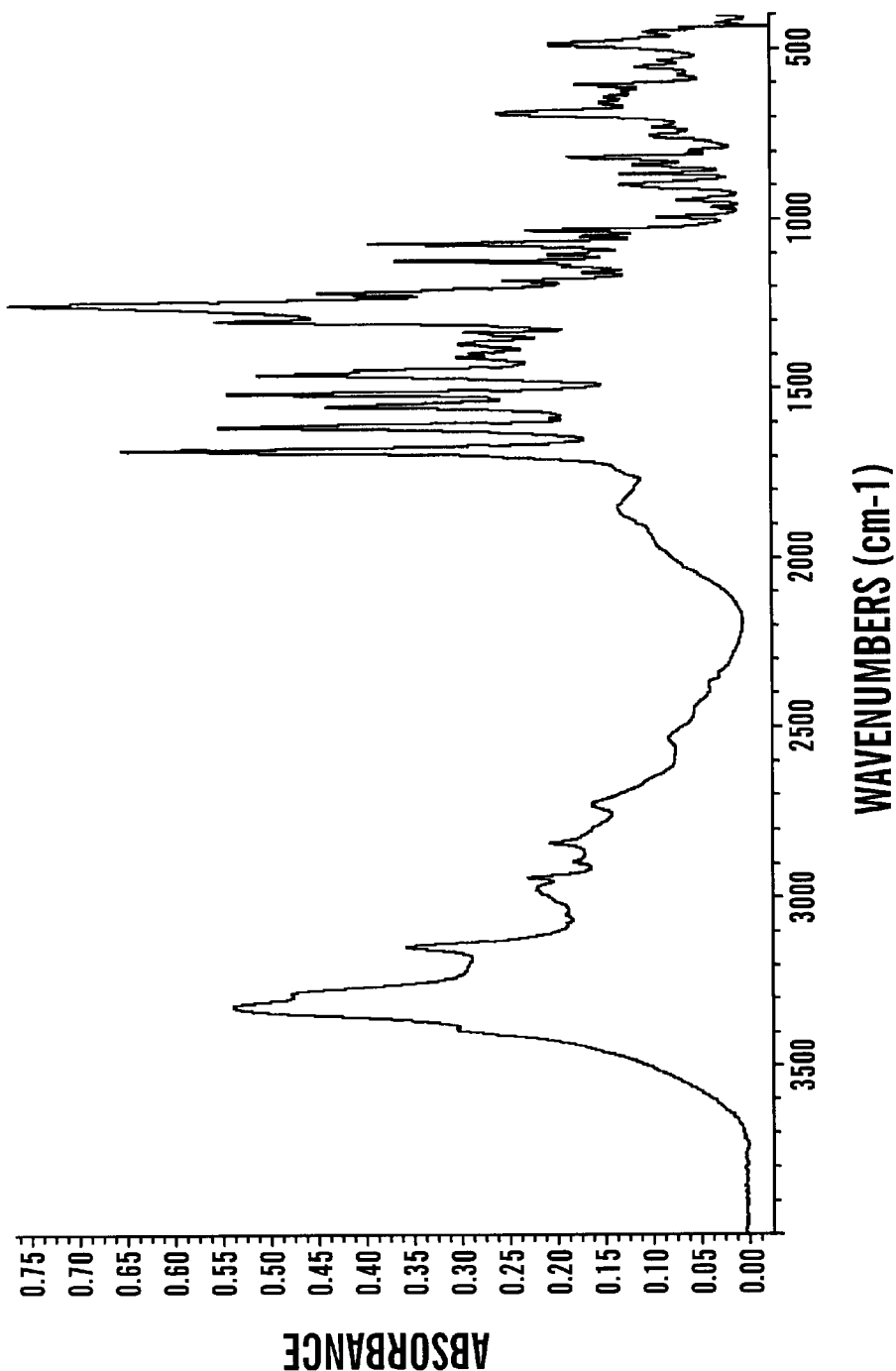
FIG. 7 is an IR spectrum of R,R-formoterol L-(+)-tartrate, polymorph A.
Figure 8:
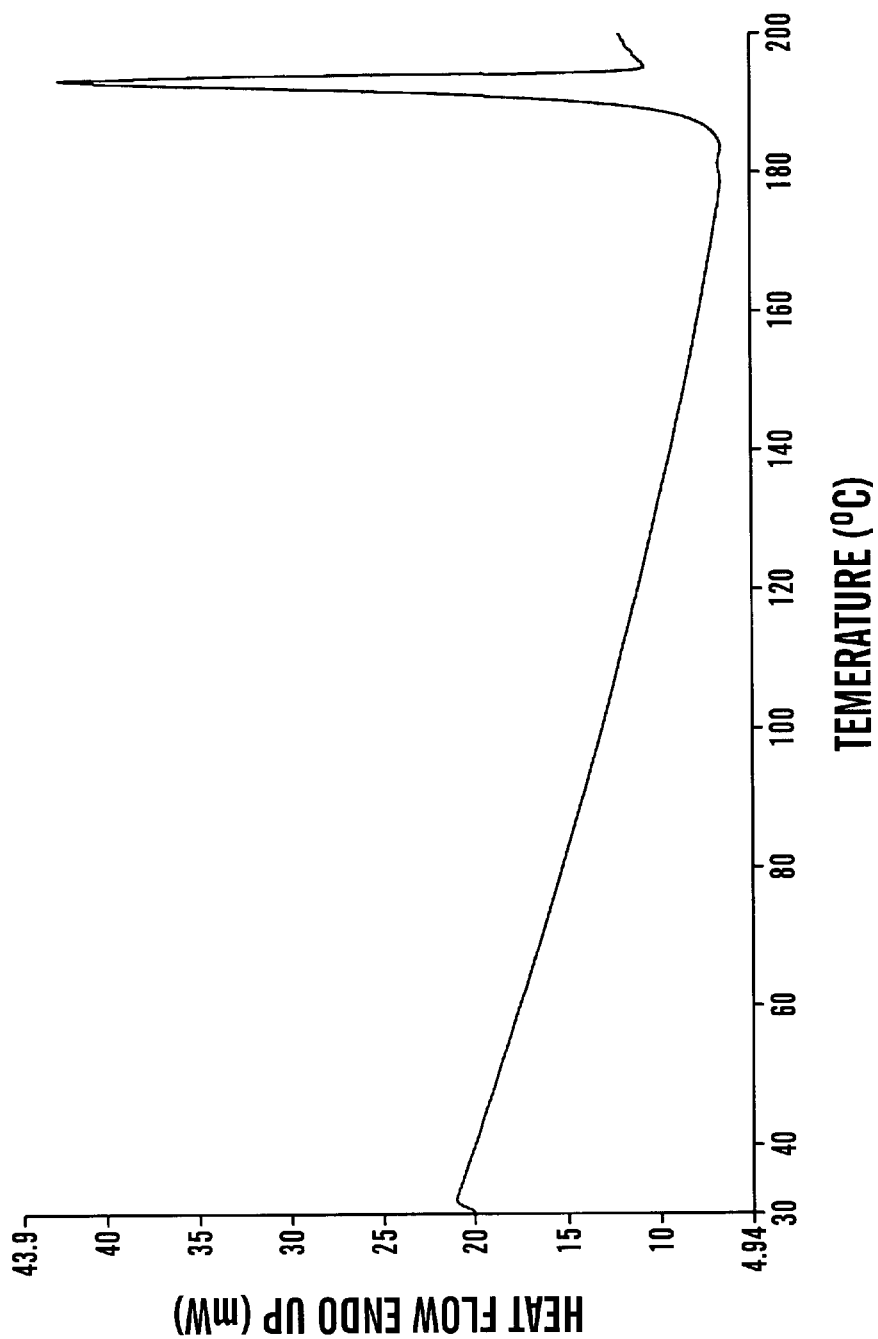
FIG. 8 is a differential scanning calorimetric (DSC) trace of R,R-formoterol L-(+)-tartrate, polymorph A.
Figure 9:
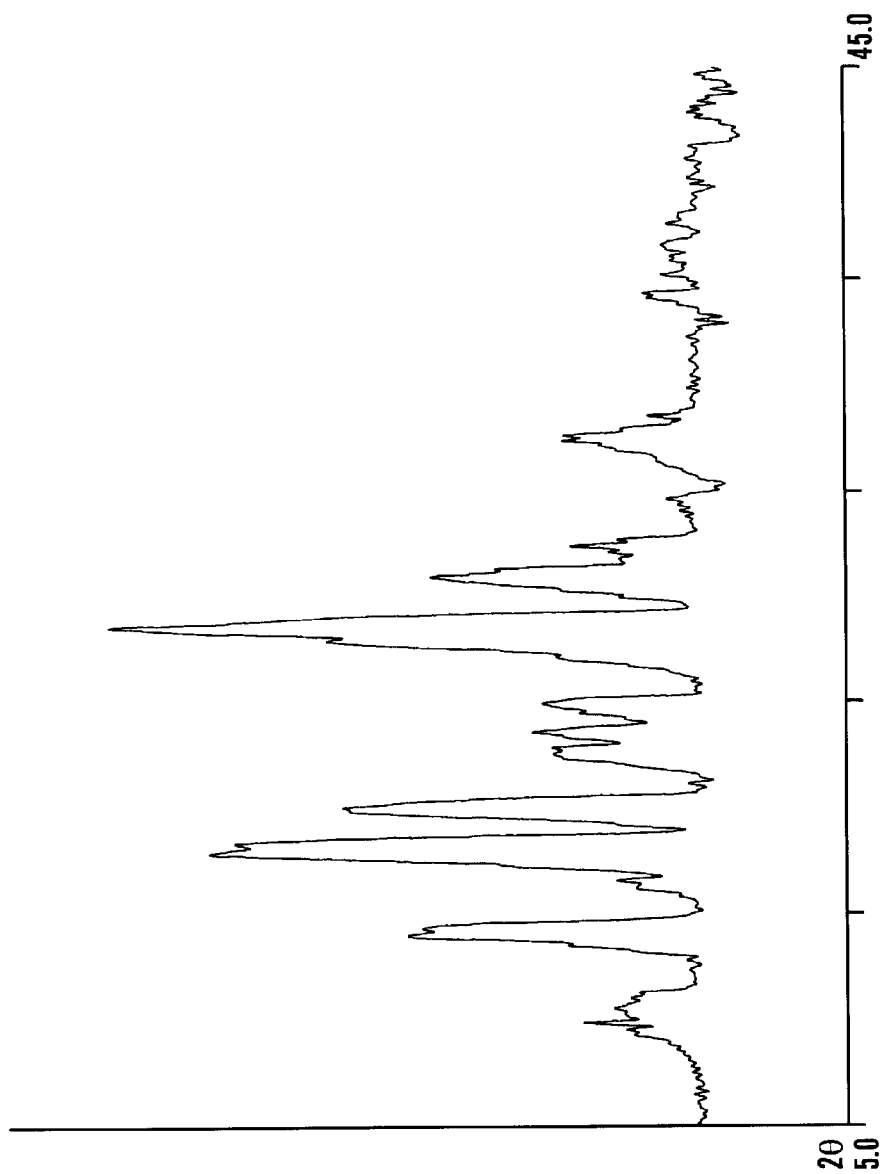
FIG. 9 is an x-ray powder diffraction pattern (XRDP) trace of R,R-formoterol L-(+)-tartrate, polymorph A.

Crystallization of polymorph B or polymorph C from aqueous isopropyl alcohol generated the same morphologically distinct solid, polymorph A. Dissolution of either crude solid in aqueous isopropyl alcohol at elevated temperatures, followed by cooling to 0–5° C. gave the crystallized solid. The IR spectrum, DSC trace, and X-ray powder diffraction pattern are shown in FIG. 3. The IR spectrum is characterized by the broad singlet at 3420 cm$^{-1}$ containing two shoulders, the singlet at 3115 cm$^{-1}$, and the broad nature of the absorbances in the 2300–3500 cm$^{-1}$ range. The DSC shows a strong, sharp endotherm transition at 192° C., and the X-ray powder diffraction spectrum contains a unique pattern. Thus B may be converted to A either directly (by a process already described in U.S. Pat. No. 6,268,533) or B may be converted to A via C by the newly discovered process. Both processes produce the same single polymorph of (R,R)-formoterol L-tartrate, uncontaminated with other polymorphic forms, but only the new process produces the single, thermodynamically most stable polymorph of (R,R)-formoterol L-tartrate in greater than 99.5% chemical purity.

The optimized process uses a controlled manipulation of the polymorphs of (R,R)-formoterol L-tartrate as the method for providing the API with <0.2% of any single impurity and in the most thermodynamically stable crystal form A.

Dissolution studies were done on each polymorph. A 17 wt % slurry of the respective solid in 50% aqueous isopropyl alcohol was stirred with warming, and the temperature of dissolution was recorded. The experiment showed that both crystal forms B and C dissolved between 49–52° C. and form A dissolved between 65–70° C. Solubility and hydrolysis in isopropyl alcohol/water mixtures were also studied. The rates of dissolution and hydrolysis were proportional to temperature and water content, as expected. A successful crystallization process, therefore, requires conditions that allow for rapid dissolution and minimal hydrolysis at the lowest temperature and lowest water content possible. The process parameters are competing because higher water concentrations allow for a lower temperature of dissolution but cause a faster rate of hydrolysis, and lower water concentrations allow for a slower rate of hydrolysis but require a higher temperature for dissolution. A solution to this paradox is found in the differential solubility of the three polymorphs.

Crystal forms B and C dissolve in aqueous isopropyl alcohol at a lower temperature than form A, form C can be generated in higher purity than form B, and form A is the most stable crystal form of the three polymorphs. Taking these factors into consideration, an optimized crystallization process has been developed (Scheme III): (1) formation of a slurry of crude polymorph B by addition of L-tartaric acid to a solution of the free-base, (2) in-situ conversion of form B to the highly pure form C, (3) isolation of crude polymorph C, (4) dissolution of form C in 50% aqueous isopropyl alcohol (50–55° C.), (5) immediate seeding of the solution with form A crystals (insoluble at 55° C. in 50% aqueous isopropyl alcohol), (6) addition of isopropyl alcohol to decrease the water content to 25% and effect a rapid cooling of the mixture to 40–45° C., and (7) cooling and isolation of the API, polymorph A. Implementation of this process reproducibly provides polymorph C with the level of any single impurity <0.1%. Although the level of 7 increases during the final crystallization (hydrolysis), the process provides the API with 7 <0.2% of 7 and <0.1% of 8.

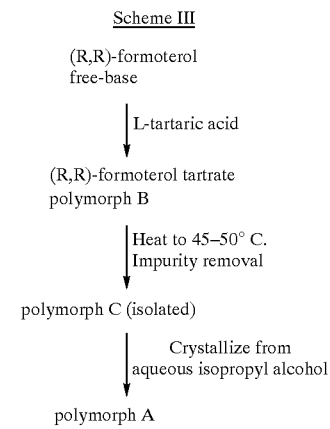

A detailed experimental procedure for the in-situ polymorph conversion/purification and crystallization processes is as follows: To 460 g of a solution of the crude (R,R)-formoterol free-base in a 3.63:1 (w/w) solution of isopropyl alcohol/toluene (approximately 164 g of (R,R)-formoterol free-base/L of solution) was added a solution of 40.8 g of L-tartaric acid in 237 g of water. The solution was stirred for 2 h, during which a slurry formed ((R,R)-FmTA crystal form B). The mixture was warmed to 45–50° C. until the level of 8 was below 0.15 A% in the solid (2–3 hr). Concomitant thickening of the slurry occurred (conversion from crystal form B to crystal form C). The mixture was cooled to 22° C., and the solid was isolated by filtration and dried to give 109 g of crude product (77% yield).

To the crude product was added 214 g of isopropyl alcohol and 272 g of water. The resultant slurry was warmed until dissolution occurred (50–55° C.). The solution was seeded with 1.1 g of crystals of polymorph A (1%), followed by 545 g of isopropyl alcohol to give a 25% (v/v) aqueous isopropyl alcohol solvent mixture. The solution immediately cooled to 40–45° C. The solution was stirred for 30 min at 40–45° C., cooled to 0° C., and stirred for 2 hr. The slurry was filtered to give 93 g (85% yield) of the API as a white solid.

What is claimed is:

1. A process for the preparation of highly pure (R,R)-formoterol L-tartrate comprising crystallizing a first polymorph (C) of (R,R)-formoterol L-tartrate from aqueous isopropyl alcohol, said first polymorph having peaks at the diffraction degrees with the intensity shown below in an X-ray powder diffraction pattern:

| Peak number | 2-Theta | Intensity |
| --- | --- | --- |
| 1 | 6.4 | 100.0 |
| 2 | 9.0 | 14.4 |
| 3 | 11.1 | 14.8 |
| 4 | 12.4 | 13.9 |
| 5 | 12.9 | 19.7 |
| 6 | 13.5 | 19.5 |
| 7 | 14.0 | 15.1 |
| 8 | 15.0 | 19.7 |
| 9 | 15.4 | 16.9 |
| 10 | 15.7 | 18.1 |
| 11 | 16.3 | 12.8 |
| 12 | 17.5 | 64.9 |
| 13 | 19.4 | 47.3 |

-continued

| Peak number | 2-Theta | Intensity |
|---|---|---|
| 14 | 19.9 | 44.8 |
| 15 | 21.3 | 29.3 |
| 16 | 22.3 | 31.5 |
| 17 | 22.9 | 35.8 |
| 18 | 24.1 | 80.0 |
| 19 | 24.7 | 17.6 |
| 20 | 25.5 | 11.3 |
| 21 | 26.0 | 15.6 |
| 22 | 26.8 | 9.1 |
| 23 | 27.4 | 8.5 |
| 24 | 28.4 | 10.8 |
| 25 | 29.0 | 8.5 |
| 26 | 30.5 | 8.1 |
| 27 | 32.7 | 10.9 |
| 28 | 34.2 | 7.9 |
| 29 | 35.7 | 9.3 |
| 30 | 36.4 | 6.6 |
| 31 | 37.3 | 7.9 |
| 32 | 37.8 | 9.1 |
| 33 | 39.3 | 10.0 |
| 34 | 39.6 | 11.4 |
| 35 | 41.1 | 5.7 |
| 36 | 42.3 | 4.7. |

2. A process according to claim 1 wherein said first polymorph is crystallized from isopropyl alcohol:water in a two stage process whereby said first polymorph is first dissolved in 50% (v/v) isopropyl alcohol:water at 50–55° C. and then immediately crystallized by seeding and addition of sufficient isopropyl alcohol to adjust to 25% (v/v)isopropyl alcohol:water.

3. A process according to claim 1 wherein:

(a) 1 part by weight of said first polymorph is dissolved, by warming, in a mixture of about 2 parts by weight isopropyl alcohol and about 2.5 parts by weight water;

(b) from 1.5 to 4 additional parts by weight of isopropyl alcohol are added;

(c) said solution is cooled; and (d) (R,R)-formoterol L-tartrate is separated from said solution.

4. A process for the preparation of a first polymorph (C) of (R,R)-formoterol L-tartrate comprising stirring a slurry of a second polymorph (B) of (R,R)-formoterol L-tartrate in water, isopropyl alcohol and from 13% to 75% by weight toluene at 40–55° C., first polymorph (C) having peaks at the diffraction degrees with the intensity shown below in an X-ray powder diffraction pattern:

| Peak number | 2-Theta | Intensity |
|---|---|---|
| 1 | 6.4 | 100.0 |
| 2 | 9.0 | 14.4 |
| 3 | 11.1 | 14.8 |
| 4 | 12.4 | 13.9 |
| 5 | 12.9 | 19.7 |
| 6 | 13.5 | 19.5 |
| 7 | 14.0 | 15.1 |
| 8 | 15.0 | 19.7 |
| 9 | 15.4 | 16.9 |
| 10 | 15.7 | 18.1 |
| 11 | 16.3 | 12.8 |
| 12 | 17.5 | 64.9 |
| 13 | 19.4 | 47.3 |
| 14 | 19.9 | 44.8 |
| 15 | 21.3 | 29.3 |
| 16 | 22.3 | 31.5 |
| 17 | 22.9 | 35.8 |
| 18 | 24.1 | 80.0 |
| 19 | 24.7 | 17.6 |
| 20 | 25.5 | 11.3 |
| 21 | 26.0 | 15.6 |
| 22 | 26.8 | 9.1 |
| 23 | 27.4 | 8.5 |
| 24 | 28.4 | 10.8 |
| 25 | 29.0 | 8.5 |
| 26 | 30.5 | 8.1 |
| 27 | 32.7 | 10.9 |
| 28 | 34.2 | 7.9 |
| 29 | 35.7 | 9.3 |
| 30 | 36.4 | 6.6 |
| 31 | 37.3 | 7.9 |
| 32 | 37.8 | 9.1 |
| 33 | 39.3 | 10.0 |
| 34 | 39.6 | 11.4 |
| 35 | 41.1 | 5.7 |
| 36 | 42.3 | 4.7. | and said second polymorph (B) having peaks at the diffraction degrees with the intensity shown below in an X-ray powder diffraction pattern:

| peak number | 2-Theta | Intensity |
|---|---|---|
| 1 | 6.7 | 29.8 |
| 2 | 7.7 | 23.9 |
| 3 | 8.5 | 76.8 |
| 4 | 9.9 | 24.1 |
| 5 | 11.6 | 23.7 |
| 6 | 12.2 | 35.9 |
| 7 | 13.0 | 24.8 |
| 8 | 13.7 | 32.7 |
| 9 | 16.4 | 32.9 |
| 10 | 17.3 | 99.1 |
| 11 | 19.4 | 47.9 |
| 12 | 20.6 | 100.0 |
| 13 | 22.1 | 72.8 |
| 14 | 22.7 | 70.2 |
| 15 | 23.5 | 29.1 |
| 16 | 23.9 | 25.0 |
| 17 | 24.5 | 22.8 |
| 18 | 25.4 | 35.8 |
| 19 | 25.5 | 39.8 |
| 20 | 26.3 | 48.0 |
| 21 | 27.4 | 25.7 |
| 22 | 28.6 | 28.6 |
| 23 | 29.5 | 20.5 |
| 24 | 30.9 | 20.1 |
| 25 | 33.0 | 19.5 |
| 26 | 37.2 | 22.1 |
| 27 | 38.6 | 20.1 |
| 28 | 40.9 | 19.7 |
| 29 | 41.7 | 20.0 |
| 30 | 44.3 | 20.0. |

5. A process according to claim 4 wherein 1 part by weight (in grams) of said second polymorph is slurried at 45–50° C. in 2.7 to 3.1 parts by volume (in milliliters) of a mixture of about 3.6 parts by weight of isopropyl alcohol, about 1 part by weight of toluene and about 0.5 parts by weight of water until the (R,R)-formoterol L-tartrate is >98% first polymorph (C).

6. A process for the preparation of a third polymorph (A) of (R,R)-formoterol L-tartrate comprising:

(a) stirring a slurry of a second polymorph (B) of (R,R)-formoterol L-tartrate in water, isopropyl alcohol and toluene at 40–55° C. to produce a first polymorph (C) of (R,R)-formoterol L-tartrate;

(b) crystallizing said first polymorph (C) of (R,R)-formoterol L-tartrate from aqueous isopropyl alcohol to produce a third polymorph (A) of (R,R)-formoterol L-tartrate; and (c) separating said third polymorph (A) of (R,R)-formoterol L-tartrate from aqueous isopropyl alcohol, said first polymorph (C) having peaks at the diffraction degrees with the intensity shown below in an X-ray powder diffraction pattern:

| Peak number | 2-Theta | Intensity |
|---|---|---|
| 1 | 6.4 | 100.0 |
| 2 | 9.0 | 14.4 |
| 3 | 11.1 | 14.8 |
| 4 | 12.4 | 13.9 |
| 5 | 12.9 | 19.7 |
| 6 | 13.5 | 19.5 |
| 7 | 14.0 | 15.1 |
| 8 | 15.0 | 19.7 |
| 9 | 15.4 | 16.9 |
| 10 | 15.7 | 18.1 |
| 11 | 16.3 | 12.8 |
| 12 | 17.5 | 64.9 |
| 13 | 19.4 | 47.3 |
| 14 | 19.9 | 44.8 |
| 15 | 21.3 | 29.3 |
| 16 | 22.3 | 31.5 |
| 17 | 22.9 | 35.8 |
| 18 | 24.1 | 80.0 |
| 19 | 24.7 | 17.6 |
| 20 | 25.5 | 11.3 |
| 21 | 26.0 | 15.6 |
| 22 | 26.8 | 9.1 |
| 23 | 27.4 | 8.5 |
| 24 | 28.4 | 10.8 |
| 25 | 29.0 | 8.5 |
| 26 | 30.5 | 8.1 |
| 27 | 32.7 | 10.9 |
| 28 | 34.2 | 7.9 |
| 29 | 35.7 | 9.3 |
| 30 | 36.4 | 6.6 |
| 31 | 37.3 | 7.9 |
| 32 | 37.8 | 9.1 |
| 33 | 39.3 | 10.0 |
| 34 | 39.6 | 11.4 |
| 35 | 41.1 | 5.7 |
| 36 | 42.3 | 4.7 | said second polymorph (B) having peaks at the diffraction degrees with the intensity shown below in an X-ray powder diffraction pattern:

| peak number | 2-Theta | Intensity |
|---|---|---|
| 1 | 6.7 | 29.8 |
| 2 | 7.7 | 23.9 |
| 3 | 8.5 | 76.8 |
| 4 | 9.9 | 24.1 |
| 5 | 11.6 | 23.7 |
| 6 | 12.2 | 35.9 |
| 7 | 13.0 | 24.8 |
| 8 | 13.7 | 32.7 |
| 9 | 16.4 | 32.9 |
| 10 | 17.3 | 99.1 |
| 11 | 19.4 | 47.9 |
| 12 | 20.6 | 100.0 |
| 13 | 22.1 | 72.8 |
| 14 | 22.7 | 70.2 |
| 15 | 23.5 | 29.1 |
| 16 | 23.9 | 25.0 |
| 17 | 24.5 | 22.8 |
| 18 | 25.4 | 35.8 |
| 19 | 25.5 | 39.8 |
| 20 | 26.3 | 48.0 |
| 21 | 27.4 | 25.7 |
| 22 | 28.6 | 28.6 |
| 23 | 29.5 | 20.5 |
| 24 | 30.9 | 20.1 |
| 25 | 33.0 | 19.5 |
| 26 | 37.2 | 22.1 |
| 27 | 38.6 | 20.1 |
| 28 | 40.9 | 19.7 |
| 29 | 41.7 | 20.0 |
| 30 | 44.3 | 20.0 | and said third polymorph (A) having peaks at the diffraction degrees with the intensity shown below in an X-ray powder diffraction pattern:

| peak number | 2-Theta | Intensity |
|---|---|---|
| 1 | 8.8 | 33.1 |
| 2 | 9.3 | 33.4 |
| 3 | 12.1 | 58.1 |
| 4 | 12.4 | 60.6 |
| 5 | 14.2 | 30.9 |
| 6 | 15.2 | 87.4 |
| 7 | 15.5 | 82.8 |
| 8 | 16.8 | 69.8 |
| 9 | 18.9 | 39.6 |
| 10 | 19.7 | 41.1 |
| 11 | 20.8 | 40.6 |
| 12 | 22.5 | 38.8 |
| 13 | 23.0 | 59.9 |
| 14 | 23.7 | 100.0 |
| 15 | 25.6 | 55.9 |
| 16 | 26.8 | 37.2 |
| 17 | 28.6 | 25.6 |
| 18 | 30.9 | 37.2 |
| 19 | 36.1 | 28.0 |
| 20 | 38.1 | 25.0 |
| 21 | 39.1 | 22.7 |
| 22 | 41.5 | 21.3 |
| 23 | 43.3 | 20.9 |

7. (R,R)-formoterol L-tartrate in the form of a crystalline solid comprising at least 95% of a first polymorph (C) having peaks at the diffraction degrees with the intensity shown below in an X-ray powder diffraction pattern:

| Peak number | 2-Theta | Intensity |
|---|---|---|
| 1 | 6.4 | 100.0 |
| 2 | 9.0 | 14.4 |
| 3 | 11.1 | 14.8 |
| 4 | 12.4 | 13.9 |
| 5 | 12.9 | 19.7 |
| 6 | 13.5 | 19.5 |
| 7 | 14.0 | 15.1 |
| 8 | 15.0 | 19.7 |
| 9 | 15.4 | 16.9 |
| 10 | 15.7 | 18.1 |
| 11 | 16.3 | 12.8 |
| 12 | 17.5 | 64.9 |
| 13 | 19.4 | 47.3 |
| 14 | 19.9 | 44.8 |

-continued

| Peak number | 2-Theta | Intensity |
| --- | --- | --- |
| 15 | 21.3 | 29.3 |
| 16 | 22.3 | 31.5 |
| 17 | 22.9 | 35.8 |
| 18 | 24.1 | 80.0 |
| 19 | 24.7 | 17.6 |
| 20 | 25.5 | 11.3 |
| 21 | 26.0 | 15.6 |
| 22 | 26.8 | 9.1 |
| 23 | 27.4 | 8.5 |
| 24 | 28.4 | 10.8 |
| 25 | 29.0 | 8.5 |
| 26 | 30.5 | 8.1 |
| 27 | 32.7 | 10.9 |
| 28 | 34.2 | 7.9 |
| 29 | 35.7 | 9.3 |
| 30 | 36.4 | 6.6 |
| 31 | 37.3 | 7.9 |
| 32 | 37.8 | 9.1 |
| 33 | 39.3 | 10.0 |
| 34 | 39.6 | 11.4 |
| 35 | 41.1 | 5.7 |
| 36 | 42.3 | 4.7. |

8. (R,R)-formoterol L-tartrate in the form of a crystalline solid consisting of greater than 99.5% by weight of formoterol L-tartrate at least 95% in the polymorphic form of a thermodynamically stable third polymorph (A) of (R,R)-formoterol L-tartrate, said polymorph (A) having peaks at the diffraction degrees with the intensity shown below in an X-ray powder diffraction pattern:

| peak number | 2-Theta | Intensity |
| --- | --- | --- |
| 1 | 8.8 | 33.1 |
| 2 | 9.3 | 33.4 |
| 3 | 12.1 | 58.1 |

-continued

| peak number | 2-Theta | Intensity |
| --- | --- | --- |
| 4 | 12.4 | 60.6 |
| 5 | 14.2 | 30.9 |
| 6 | 15.2 | 87.4 |
| 7 | 15.5 | 82.8 |
| 8 | 16.8 | 69.8 |
| 9 | 18.9 | 39.6 |
| 10 | 19.7 | 41.1 |
| 11 | 20.8 | 40.6 |
| 12 | 22.5 | 38.8 |
| 13 | 23.0 | 59.9 |
| 14 | 23.7 | 100.0 |
| 15 | 25.6 | 55.9 |
| 16 | 26.8 | 37.2 |
| 17 | 28.6 | 25.6 |
| 18 | 30.9 | 37.2 |
| 19 | 36.1 | 28.0 |
| 20 | 38.1 | 25.0 |
| 21 | 39.1 | 22.7 |
| 22 | 41.5 | 21.3 |
| 23 | 43.3 | 20.9. |

9. A method for preventing bronchoconstriction or inducing bronchodilation in a mammal comprising administering to said mammal a therapeutically effective amount of the solid R,R-formoterol L-(+)-tartrate of claim 8.

10. A pharmaceutical composition comprising a pharmaceutically acceptable carrier and the solid R,R-formoterol L-(+)-tartrate of claim 8.

11. An aerosol pharmaceutical composition according to claim 10.

12. An oral pharmaceutical composition according to claim 10.

13. An oral pharmaceutical composition according to claim 12 in the form of a tablet, capsule or syrup.

14. A dry powder pharmaceutical composition for inhalation according to claim 10.

\* \* \* \* \*

UNITED STATES PATENT AND TRADEMARK OFFICE
CERTIFICATE OF CORRECTION

PATENT NO.       : 6,472,563 B1
APPLICATION NO.  : 10/037183
DATED            : October 29, 2002
INVENTOR(S)      : Tanoury et al.

Page 1 of 1

It is certified that error appears in the above-identified patent and that said Letters Patent is hereby corrected as shown below:

Claim 2, Col. 13, Line 31: Delete "adjust to 25%" and insert -- adjust to 75% --

Signed and Sealed this

Third Day of February, 2009

JOHN DOLL
*Acting Director of the United States Patent and Trademark Office*